United States Patent [19]

Richman

[11] Patent Number: 5,108,556

[45] Date of Patent: Apr. 28, 1992

[54] PROCESS FOR PREPARING TERTIARY PERFLUOROAMINES

[75] Inventor: Jack E. Richman, Oakdale, Minn.

[73] Assignee: Minnesota Mining and Manufacturing Company, St. Paul, Minn.

[21] Appl. No.: 582,675

[22] Filed: Sep. 14, 1990

[51] Int. Cl.$^5$ .................... C25B 3/06; C07C 19/08
[52] U.S. Cl. .................... 204/59 F; 204/81; 570/124; 570/140
[58] Field of Search .................... 204/81, 59 F, 59 R; 570/123, 124, 140

[56] References Cited

U.S. PATENT DOCUMENTS

| | | | |
|---|---|---|---|
| 2,519,983 | 8/1950 | Simons | 204/59 R |
| 2,567,011 | 9/1951 | Diesslin et al. | 560/227 |
| 2,616,927 | 11/1952 | Kauck et al. | 564/462 |
| 3,028,321 | 4/1962 | Danielson | 204/59 R |
| 3,692,643 | 9/1972 | Holland | 204/59 R |
| 4,686,024 | 8/1987 | Scherer et al. | 204/157.95 |

OTHER PUBLICATIONS

Young et al., "Fluorocarbon Nitrogen Compounds, I. Perfluorocarbamic Acid Derivatives, Amides and Oxazolidines", *J. Amer. Chem. Soc.*, vol. 78, pp. 5637–5639 (1956).

L. Conte et al., "Correlation Between Yield and Operating Conditions in the Electrochemical Fluorination of Tripropylamine", *J. of Fluorine Chemistry*, 30, (1985), pp. 89–95.

L. Conte et al., "Electrochemical Fluorination of Some Cyclic Tertiary Amines", *J. of Fluorine Chemistry*, 34 (1986), pp. 183–189.

J. A. Young, "Fluorocarbon Nitrogen Compounds, II. The Synthesis and Properties of Perfluorodimethylglycine, (CF$_3$)$_2$NCF$_2$COOH", *J. Am. Chem. Soc.*, 80 (1958), pp. 1889–1892.

R. J. Harder et al., "Chemistry of Sulfer Tetrafluoride, VI. Fluorination of Thiocarbonyl Compounds", *J. Am. Chem. Soc.*, 83 (1961), pp. 3422–3424.

P. Chabrier et al., *Bull. Chim. Soc. Fr.*, 1950, pp. 1166–1175.

"Organic Electrochemistry", Second Edition, Revised and Expanded, Marcel Dekker, Inc., New York and Basel.

*Primary Examiner*—John Niebling
*Assistant Examiner*—Steven P. Marquis
*Attorney, Agent, or Firm*—Gary L. Griswold; Walter N. Kirn; Carole Truesdale

[57] ABSTRACT

A process for preparing tertiary perfluoroamines is provided. The process comprises electrochemically fluorinating a tertiary thioamide precursor, said thioamide precursor having at least one thioamide moiety,

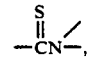

and terminal portions which can be alkyl or cycloalkyl having 1 to 12 carbon atoms, aryl having 6 to 12 carbon atoms, or combinations thereof, with the proviso that when more than one thioamide moiety is present, the thioamide moieties are bonded together by alkylene, cycloalkylene or arylene groups. Also provided are tertiary thioamides and tertiary perfluoroamines.

22 Claims, No Drawings

PROCESS FOR PREPARING TERTIARY PERFLUOROAMINES

This invention relates to a process for preparing tertiary perfluoroamines.

Tertiary perfluoroamines are normally liquid and have a wide liquid range, including boiling points up to about 300° C. and pour points as low as 0° C. or less. These perfluoroamines have utility as hydraulic fluids, heat transfer fluids, pump fluids for corrosive environments, and fluids for vapor phase condensation heating for soldering and polymer curing applications.

Tertiary perfluoroamines have been prepared from corresponding hydrocarbon tertiary amines, such as tri-pentafluoroethylamine, $(C_2F_5)_3N$, from triethylamine, $(C_2H_5)_3N$, by electrochemical fluorination conducted in liquid hydrogen fluoride as disclosed in U.S. Pat. No. 2,519,983 (Simons) and 2,616,927 (Kauck et al.). However, as Kauck et al. state, this electrochemical process produces as by-products various fragmentation products containing fewer carbon atoms than the parent compound, due to cleavage of carbon-nitrogen and even carbon-carbon bonds in the case of some molecules and by-products consisting of fluorocarbon tertiary amine compounds which contain a greater number of carbon atoms and which have higher boiling points than the fluorocarbon tertiary amine which corresponds to the starting compound which are presumably formed by the combining of free radicals in the electrolyte solution.

L. Conte et al. "Correlation Between Yield and Operating Conditions in the Electrochemical Fluorination of Tripropylamine," *J. of Fluorine Chemistry*, 30(1985) pp 89–95, discloses that the electrochemical fluorination process generally exhibits low yields of perfluorinated tertiary amines. The reported yield for perfluorinated tertiary amines include triethylamine: 27%, tripentylamine: 25%, and tributylamine: 18%. Conte et al. report that such low yields are principally due to side reactions of degradation and rearrangement that are usual in electrochemical fluorination and to an incomplete substitution of hydrogen atoms by fluorine in the organic molecule In the electrochemical fluorination of tripropylamine, Conte et al. found that the yield was influenced by operating conditions with the most marked changes in yield being caused by the initial concentration of the amine and especially by temperature.

L. Conte et al. "Electrochemical Fluorination of Some Cyclic Tertiary Amines", *J. of Fluorine Chemistry*, 34 (1986) pp 183–189 discloses electrochemical fluorination of N,N-diethylcyclohexylamine and N-ethyldicyclohexylamine to give the corresponding F-amines, i.e., perfluoroamines, together with several other compounds arising from incomplete fluorination and fragmentation reactions.

Electrochemical fluorination of dimethylcarbamyl chloride, dimethylformamide, diethylcarbamyl chloride, dimethylacetamide, dimethyltrifluoroacetamide, morpholinocarbonyl chloride, and tetramethylurea to yield bis-(trifluoromethyl) carbamyl fluoride has been disclosed by J. A. Young et al. in "Fluorocarbon Nitrogen Compounds. I. Perfluorocarbamic Acid Derivatives, Amides and Oxazolidines," *J Am. Chem. Soc.*, 78 (1956) pp 5637–5639. Young et al. report that with all the starting compounds there is considerable fragmentation.

Electrochemical fluorination of both the methyl ester and N,N-dimethylamide of dimethylglycine to yield perfluorodimethylglycine has been reported by J. A. Young et al. in "Fluorocarbon Nitrogen Compounds. II. The Synthesis and Properties of Perfluorodimethylglycine, $(CF_3)_2NCF_2COOH$," *J Am. Chem. Soc.*, 80 (1958), pp 1889–1892.

R. J. Harder et al., "Chemistry of Sulfur Tetrafluoride, VI. Fluorination of Thiocarbonyl Compounds," *J. Am. Chem. Soc.*, 83 (1961), pp 3422–3424, discloses fluorination of thiocarbonyl groups with sulfur tetrafluoride to convert the thiocarbonyl groups, —C(S)—, to perfluoromethylene groups, —CF_2—. This type of mild fluorination is not capable of perfluorinating hydrocarbon groups.

U S. Pat. No. 3,692,643 (Holland) discloses that the presence of a small amount of a thioester of aromatic or aliphatic carboxylic acids in the electrolyte during the electrochemical fluorination of alkyl substituted or unsubstituted, aromatic or aliphatic, sulfonic or carboxylic acid halides decreases the rate of electrode decomposition, raises the yield of perfluorinated product and decreases the formation of viscous materials.

The present invention relates to a process for preparing tertiary perfluoroamines comprising electrochemically fluorinating a tertiary thioamide precursor. The tertiary thioamide precursor, hereinafter "thioamide," comprises at least one thioamide moiety,

and terminal portions which can be alkyl or cycloalkyl having 1 to 12 carbon atoms, preferably 2 to 6 carbon atoms or aryl having 6 to 12 carbon atoms, e.g., phenyl, which terminal hydrocarbon portions may contain catenary oxygen, i.e., oxygen atom in the chain or ring between two carbon atoms. When more than one thioamide moiety is present, the moieties are bonded together by alkylene or arylene linking groups or combinations thereof. Preferably at least three carbon atoms are present between the nitrogen atoms of the thioamide moieties. As is well known in the art, compositions such as these tertiary thioamide percursors often exist as mixtures with dimers or higher oligomers in equilibrium with the desired precursor compounds.

The present invention also relates to novel tertiary thioamides and novel tertiary perfluoroamines. Such novel compounds include

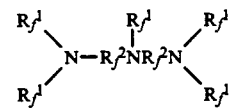

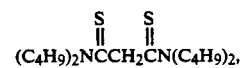

and

-continued $$C_nX_{2n+1} \diagdown \underset{\underset{C_{n'}H_{2n'+1}}{\diagup}}{\overset{S}{\overset{\|}{C}}} NC_aH_{2a} \left[ N \left( \overset{S}{\underset{\|}{C}}C_nX_{2n+1} \right) C_aH_{2a} \right]_b \overset{S}{\underset{\|}{N}}C \diagdown \underset{C_{n'}H_{2n'+1}}{\overset{C_nX_{2n+1}}{\diagup}}$$

Wherein each $R_f^1$ is independently perfluoroalkyl, a fluorinated, stable, inert, non-polar, preferably saturated, monovalent moiety which is both hydrophobic and oleophobic, and can be straight chain, branched chain or, if sufficiently large, cyclic or combinations thereof, such as alkylcycloaliphatic, and can include catenary divalent oxygen atoms and/or trivalent nitrogen atoms bonded only to carbon atoms or two $R_f^1$ groups attached to the same nitrogen atom can be joined to form a ring having 4 to 10 carbon atoms, and $R_f^1$ generally has 1 to 12 carbon atoms, preferably 3 to 12 carbon atoms, and contains about 60 to 83 weight percent, preferably 74 to 83 weight percent, carbon-bound fluorine; $R_f^2$ is a perfluoroalkylene, perfluorocycloalkylene or combinations thereof having 1 to 10 carbon atoms which can contain one or more tertiary amino groups.

X is H or F, each n and n' are independently integers of from 1 to 10, a is an integer of from 1 to 10, and b is 0, 1 or 2.

The advantages of the process of the present invention, the use of tertiary thioamides as precursors for tertiary perfluoroamines, compared to the electrochemical fluorination of hydrocarbon tertiary amines, may include ease of preparation, reduced cost, improved yields as a result of reduced skeletal isomerization, cleavage, and radical recombination, and improved thermal and/or chemical stability.

Although the thioamide precursors used in the process of this invention are generally fluorine-free, partially fluorinated tertiary thioamides can be electrochemically fluorinated and in some cases provides ease of synthesis of the thioamide, reduced rearrangement and cleavage of the hydrocarbon portion of the molecule during fluorination, and the absence of rearrangement and cleavage in the fluorocarbon portion of the molecule during fluorination.

The transformation which occurs during electrochemical fluorination (ECF) of the thioamides can be represented, for example, by the following schemes.

$$R^1-\overset{S}{\underset{\|}{C}}N\diagdown \underset{R^1}{\overset{R^1}{\diagup}} \xrightarrow{\text{HF}}_{\text{ECF}} R_f^1-CF_2N\diagdown \underset{R_f^1}{\overset{R_f^1}{\diagup}} + SF_6$$

or $$R^1\diagdown \underset{R^1}{\overset{S}{\underset{\|}{N}}}C-R^2-\overset{S}{\underset{\|}{C}}N\diagdown \underset{R^1}{\overset{R^1}{\diagup}} \xrightarrow{\text{HF}}_{\text{ECF}}$$

$$R_f^1\diagdown \underset{R_f^1}{\overset{}{\diagup}}NCF_2-R_f^2-CF_2N\diagdown \underset{R_f^1}{\overset{R_f^1}{\diagup}} + 2SF_6$$

or $$R^1-\overset{S}{\underset{\|}{C}}N\diagdown \underset{R^3}{\overset{R^3}{\diagup}}\diagdown \overset{S}{\underset{\|}{N}}CR^1 \xrightarrow{\text{HF}}_{\text{ECF}}$$

$$R_f^1CF_2N\diagdown \underset{R_f^3}{\overset{R_f^3}{\diagup}}\diagdown NCF_2R_f^1 + 2SF_6$$

or $$R^1\diagdown \underset{R^1}{\overset{S}{\underset{\|}{C}}}NR^3\left[N\left(\overset{S}{\underset{\|}{R^1C}}\right)R^3\right]_b N\left(\overset{S}{\underset{\|}{R^1C}}\right)R^1 \xrightarrow{\text{HF}}_{\text{ECF}}$$

$$R_f^1\diagdown \underset{R_f^1}{\overset{}{\diagup}}CF_2NR_f^3\left[N\left(R_f^1CF_2\right)R_f^3\right]_b N\left(R_f^1CF_2\right)R_f^1 +$$

$$b + 2SF_6$$

wherein each $R^1$ is independently alkyl, cycloalkyl, aryl or a combination thereof which can contain catenary oxygen atoms or two $R^1$ groups attached to the same nitrogen atom can be joined to form a ring having 4 to 10 carbon atoms and which can contain a catenary oxygen atom;

$R^2$ is an alkylene, cycloalkylene, arylene or combination thereof having 1 to 10 carbon atoms which can contain one or more tertiary nitrogen atoms;

$R^3$ is alkylene containing 1 to 10, preferably 3 to 6 carbon atoms;

$R^1$ and $R_f^2$ are as previously defined;

$R_f$ is perfluoroalkylene containing 1 to 10 carbon atoms, preferably 3 to 6 carbon atoms, and b is 0, 1 or 2.

As can be seen from the scheme, cleavage of the carbon-sulfur bond leads to loss of the sulfur atom of the thiocarbonyl group as $SF_6$ and fluorination of the carbon atom to form a perfluoromethylene group.

Additional examples of precursors useful in the present invention include:

$$C_nH_{2n+1}\overset{S}{\underset{\|}{C}}N\diagdown \underset{C_{n''}H_{2n''+1}}{\overset{C_{n'}H_{2n'+1}}{\diagup}}$$

wherein n, n', and n" are independently integers of from 1 to 10;

$$(C_nH_{2n+1})_xC_6H_y\overset{S}{\underset{\|}{C}}N\diagdown \underset{C_{n''}H_{2n''+1}}{\overset{C_{n'}H_{2n'+1}}{\diagup}}$$

wherein n, n', and n" are independently integers of from 1 to 10; x is 0 to 5; y is 0 to 5; and x+y is 5;

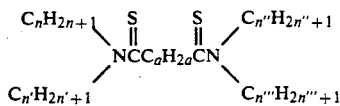

wherein n, n', n", and n'" are independently integers of from 1 to 10 and a is an integer of from 1 to 10;

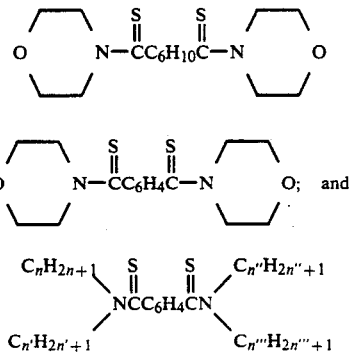

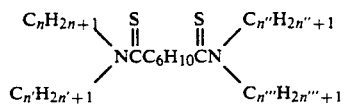

wherein n, n', n", and n'" are independently integers of from 1 to 10;

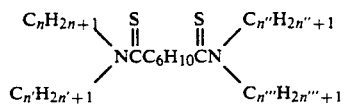

wherein n, n', n", and n'" are independently integers of from 1 to 10;

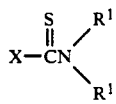

wherein X is H or f, and $R^1$ is as defined above;

wherein $R^1$ is as defined above and $R^3$ is alkylene containing 1 to 10 carbon atoms, preferably 3 to 6 carbon atoms;

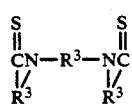

wherein each $R^3$ is alkylene containing 1 to 10, preferably 3 to 6 carbon atoms;

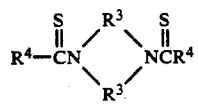

wherein $R^3$ and $R^4$ are as defined above;

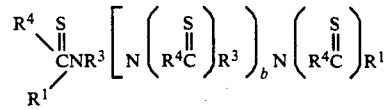

wherein $R^1$, $R^3$, and b are as defined above and $R^4$ is H, F or $R^1$;

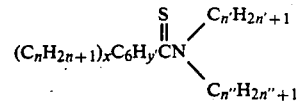

wherein n, n', and n" are independently integers of from 1 to 10; x is 0 to 5; y' is 0 to 11; and x+y' is 11;

The conversion of organic compounds to perfluorinated derivatives by electrochemical fluorination is described, for example, in U.S. Pat. Nos. 2,519,983 (Simons) and 2,567,011 (Simons et al.). The precursor thioamides may also be electrochemically fluorinated using organic conductivity additives as described in U.S. Pat. No. 3,028,321 (Danielson). Thus, further details on the method of electrochemical fluorination used to perfluorinate tertiary thioamides to obtain tertiary perfluoroamines will be omitted in the interest of brevity and these patents are incorporated herein by reference for such details.

As is well known, the liquid electrochemical fluorination process produces product mixtures of perfluorinated materials related to the original organic precursor skeletal structure, including products resulting from one or more isomerization, cleavage, or recombination reactions. Thus, in a boiling range corresponding to the desired product, it is usual to find a host of related perfluorinated compounds. Generally, separation and/or identification of these compounds is extremely difficult and not necessary for the use of the products. Generally, the desired perfluoroamine material comprises the major component, e.g., as high as 60 weight percent or more of the product mixture, indicating the unusually favorable electrochemical fluorination behavior of the thioamide precursors. In some cases considerable structural reorganization of the precursor occurs during fluorination, as indicated by boiling points both lower and higher than expected and by fluorine nuclear magnetic reasonance, $^{19}$F-nmr, and gas chromatography-mass spectrometry, gc-ms, analyses. Lower molecular weight cleavage products as well as the higher molecular weight materials also may be useful perfluorinated amine compositions.

The perfluoroamine compositions can contain a small amount of hydrogen due to incomplete fluorination. The amount of hydrogen retained generally ranges from less than 0.005 mg/g to as much as 1.5 mg/g. Purification of the product, i.e., removal of partially fluorinated products and carboxylic acid fluoride by-products, can be carried out, for example, by boiling the product with aqueous alkaline solution, a well-known technique in the art. Fluorination stabilization can be carried out prior to treatment with the aqueous alkaline solution using methods such as those taught in U.S. Pat. No. 4,686,024 (Scherer et al.).

This invention is further illustrated by the following examples, but the particular materials and amounts thereof recited in these examples, as well as other conditions and details, should not be construed to unduly limit this invention. In the following examples, the propyl and butyl groups are n-propyl and n-butyl groups and all parts and percentages are by weight unless otherwise indicated.

EXAMPLE 1

Freshly distilled di-n-propylamine was converted to the trifluoroacetate salt. This salt (607 g, 2.82 moles) was charged into a 3-L, 3-necked flask with mechanical stirrer and Dry-ice condenser. Trifluoroacetic anhydride (737 g) was added to the flask. The contents of the flask warmed spontaneously to a gentle reflux and became homogeneous in about 10 minutes. Stirring was continued for hours and refluxing was carried out for 3 hours. Additional trifluoroacetic anhydride (78 g) was added and the mixture stirred and refluxed overnight. The resulting reaction product was distilled starting at atmospheric pressure and then at reduced pressure, reaching 10 mm, to provide 600 g trifluoroacetic acid. The product was washed with water and the pH adjusted to 7 using sodium hydroxide. This amide was then dried with magnesium sulfate, filtered, combined with ether washings and distilled at atmospheric pressure giving 510 g N,N-dipropyltrifluroacetamide, a clear, colorless liquid.

A 3 L 3-necked flask was charged with 480 g of phosphorus pentasulfide ($P_4S_{10}$) and 471 g of N,N-dipropyltrifluoroacetamide. This mixture was mechanically stirred and heated slowly to 212° C. The reaction mixture was black and a sample obtained by distillation showed no carbonyl absorption when examined by infrared spectroscopy. The reaction mixture was cooled to room temperature. The liquid phase was decanted and combined with methylene chloride washes of the solids, and distilled at 2 Torr pressure. The resulting yellow-orange thioamide product, 459 g N,N-dipropyltrifluorothioacetamide,

had a boiling range of 75°-77° C./2 Torr. The infrared spectrum of the thioamide was consistent with this product.

Electrochemical fluorination of 454 g of the N,N-dipropyltrifluorothioacetamide produced 658.5 g of cell drainings. $SF_6$ gas generation was identified by infrared spectroscopy of the volatilized gases. Analysis of the $^{19}F$-nmr spectrum indicated that perfluoro(ethyldi-n-propylamine), $CF_3CF_2N(C_3F_{76})_2$, was present as the major component, about 60% of the total. Minor products were $C_7F_{17}N$ and $C_6F_{15}N$, products of C—C bond cleavages.

EXAMPLE 2

N,N-dipropylacetamide (504 g, 3.52 moles) was stirred in 1 L of dry acetonitrile under nitrogen atmosphere as 445.5 g of $P_4S_{10}$ was added in small portions. The reaction temperature was maintained at 55°-65° C. during the addition (spontaneous exotherm at first). This mixture was poured into 1 L of water containing 160 g of sodium hydroxide. The dark organic phase was washed twice with water then was diluted with 500 mL of ether and 3 L of petroleum ether (b.p. 30°-60° C. A black oil separated. The ether phase was dried (MgSO$_4$), concentrated and distilled under vacuum giving 272 g of deep yellow-orange thioamide (b.p. 95°-115° C./1.1 Torr). On standing exposed to air, the thioamide darkened to reddish black. Analysis by infrared and nmr spectroscopy confirmed that the resulting product was N,N-dipropylthioacetamide,

Electrochemical fluorination of 272 g of the N,N-dipropylthioacetamide produced 659.2 g of cell drainings. $SF_6$ gas generation was identified by infrared spectroscopy of the volatilized gases. Analysis of the reaction product by $^1H$ and $^{19}F$ nuclear magnetic resonance (nmr) confirmed the presence of perfluoro(ethyldi-n-propylamine, $CF_3CF_2N(C_3F_7)_2$. A few trace peaks in the $^{19}F$-nmr spectra of the product prepared from N,N-dipropylthioacetamide were absent in the corresponding spectra in Example 1. All of the major peaks and most of the minor (even trace) peaks were present in the spectra for each of the fluorinated products. Relative intensities of the peaks varied somewhat. The calculated yield of fluorinated products having 6-8 carbon atoms was 67%.

EXAMPLE 3

To a cooled solution of 300 g of sodium hydroxide, 327.8 g of 3,3,-iminobispropylamine (Aldrich Chemical Co.) and 1 L of water, a solution of 1430 g of toluenesulfonyl chloride in 2 L of methylene chloride was slowly added while maintaining the temperature at 0° to 10° C. After two hours stirring at 25° C. the aqueous phase was neutral at pH 7. The lower phase was concentrated under reduced pressure and diluted with absolute ethanol to induce crystallization. A total of 1377 g (m.p. 108°-110° C, 93% yield) of N,N-bis-(3-p-toluenesulfonamidopropyl)-p-toluenesulfonamide was collected by filtration. The corresponding disodium salt was prepared in 98% yield by dissolving 535 g of the sulfonamide in 2.3 L of 0.78 M sodium ethoxide/ethanol and collecting the resulting precipitate by filtration.

A slurry of 319 g of the disodium salt of N,N-bis-(3-p-toluenesulfonamidopropyl)-p-toluenesulfonamide in 900 g of dimethylformamide (DMF) was heated until homogeneous. The resulting solution was then cooled to 100° C. and stirred as a solution of 150 g of 1-chloropropane in 300 mL of DMF was added over 1-2 hours. This mixture was heated an additional hour at 100° C., then it was cooled and diluted with water. The organic phase was separated, washed with water and concentrated at 70°-85° C/1 Torr to 332 g of crude product that crystallized on addition of methanol giving 250 g of 4,8,12-tris-(p-toluenesulfonyl)-4,8,12-triazapentadecane, m.p. 80°-83° C.

A solution of 10.0 g of the 4,8,12-tris-(p-toluenesulfonyl)-4,8,12-triazapentadecane in 20 mL of concentrated sulfuric acid was heated two days at 110°-125° C. Water (16 g) was carefully added to 32 g (70%) of the resulting solution. Slow cooling of the resulting solution produced a crystalline mass from which the solids (3.9 g of a mixture of hydrates of the sulfate and hydrosulfate salts of 4,8,12-triazapentadecane) were isolated by filtration and washed with ethanol. Conversion to the trihydrochloride salt was achieved by adding aqueous barium chloride solution to a solution of the sulfate/bisulfate salt in warm water. Barium sulfate was removed by filtration and the mother liquor was concentrated to 0.75 g of crystalline 4,8,12-triazapentadecane trihydrochloride.

To determine the boiling point, the anhydrous free base of this amine was isolated by treating the crude sulfate/bisulfate salt or the trihydrochloride salt with aqueous base and extracting the free base into methylene chloride or toluene. Distillation and vacuum distillation of the resulting organic solution gave the free base, a colorless liquid boiling 90°–103° C/0.2 Torr. Exposure of this anhydrous liquid amine to air produced a solid hydrate.

The trihydrochloride salt was treated with excess trifluoroacetic anhydride to produce 4,8,12-tris-(trifluoroacetyl)-4,8,-12-triazapentadecane in good yields (70–100%). The by-product acids (hydrochloric and trifluoroacetic) were removed by distillation. Washing of the product with aqueous base led to partial hydrolysis of amide linkages.

Thus, for example, 0.54 g of 4,8,12-triazapentadecane trihydrochloride was refluxed 4.5 hours with 6 mL of trifluoroacetic anhydride. The resulting mixture was cooled and trifluoroacetic acid and anhydride were removed under reduced pressure. The residue was distilled bulb-to-bulb (evaporative distillation) at 165° C./0.13 Torr giving 0.83 g (92% yield) of 4,8,12-tris(trifluoroacetyl)-4,8,12-triazapentadecane, a clear colorless oil.

A slurry of 10.0 g of $P_4S_{10}$ and 4.09 g (7.7 mmol) of 4,8,12-tris(trifluoroacetyl)-4,8,12-triazapentadecane in 50 mL of dry acetonitrile was refluxed 21 hours until infrared spectroscopy showed that no more carbonyl amide groups remained. The reaction mixture was black Acetonitrile was removed under vacuum and the residue was dissolved in $CHCl_3$, filtered and concentrated (8 g). This residue was triturated with 50 mL of benzene. The filtered benzene solution was concentrated to 5.7 g of dark orange oil. This oil was then extracted four times with 50 mL hot hexane. The hexane extracts, concentrated to 3.9 g of yellow residue, were shown by nmr to contain 29 mole % (14 wt %) of $(EtO)_3PS$ formed by reaction of ethanol in the initial $CHCl_3$ extract solvent with $P_4S_{10}$ residues. Distillation of this oil gave 0.44 g of forerun [mainly $(EtO)_3PS$] and 3.03 g (67% yield of viscous dark amber oil distilling at 165° C./0.1 Torr in a bulb-to-bulb apparatus. This oil was substantially pure (>95%) 4,8,12-tris-trifluorothioacetyl)-4,8,12-triazapentadecane,

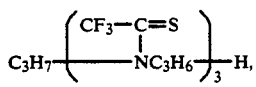

thioamide product with only a trace of amide contaminate. Samples of this thioamide purified by silica chromatography were bright yellow.

Electrochemical fluorination of 183 g of 4,8,12-tris(-trifluorothioacetyl)-4,8,12-triazapentadecane gave a total of 147 g, of colorless fluorocarbon cell drainings. The crude cell drainings were treated with sodium fluoride to remove HF and gas chromatographic (g.c) analyses were done using a ⅛ in.×12 ft. (0.32 cm×3.64 m) Porosil C. column with thermoconductivity detection and linear temperature programmed operation with He carrier gas. The analyses showed that the percentage of the peak

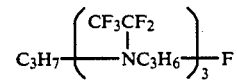

and isomers thereof reached a maximum of 24% of the total integral in the second drainings and dropped considerably (to 10%) in the third drainings. Proton nmr of these crude cell drainings showed a normal amount of residual hydrogen. The second crude cell drainings, 22.5 g, were distilled. The resulting colorless oily product was fractionated. Those fractions boiling between 111°–136° C. and 136°–142° C. at 9 Torr and between 101°–121° C. at 0.2 Torr were collected.

Those fractions contained the components that gave peaks corresponding to

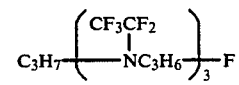

and isomers thereof on g.c. analyses.

The fraction boiling between 136°–142° C. at 9 Torr was treated by refluxing with an aqueous alkaline solution to effect removal of partially fluorinated products. Gas chromatography on this product showed the major component corresponded to

and closely related structures. This identity was confirmed by mass spectroscopy using ms/ms analyzers. Mass spectroscopy (ms) also showed that monocyclic and bicyclic compounds, $C_{18}F_{39}N_3$ and $C_{18}F_{37}N_3$, were present and eluted with the acyclic product. Proton nmr showed essentially no hydride remained in the perfluoroamine. Fluorine nmr ($F^{19}$) was consistent with the expected perfluoroamine structure as the major component:

From the g.c. retention time, the boiling point of the major components in this material (including mono- and bicyclics) was estimated as 250°–270° C. The bulk sample (which contained 15–20% of a second lower boiling component, probably $C_{17}F_{39}N_3$ or $C_{16}F_{37}N_3$) was a viscous fluid at $-10°$ C. From this behavior, the pour point of the bulk sample was estimated to be $-10$ to $-15°$ C.

EXAMPLE 4

Tetrapropylmalonamide was prepared in 63% yield from dimethyl malonate and dipropylamine (HCl catalyst). Dithiophosphorylanisole dimer $(ArPS_2)_2$, Lawesson's reagent, was prepared by heating and stirring 800 mL of anisole and 8 g (0.72 mol) of $P_4S_{10}$ at gentle reflux with caustic trapping of evolved $H_2S$. The gas evolution was nearly complete after 2½ hours but the resulting slurry was maintained at 100° C. overnight. The slurry was cooled to 20° C. and 634 g (0.43 mol) of tetrapropylmalonamide was added in one portion. The solids rapidly dissolved and the mixture was heated at 125° C. for 3 hours, then overnight at 100° C. Additional Lawesson's reagent (from 24 g P$_4$S$_{10}$) was added and heating at 100° C. continued for an additional 20 hours. The reaction mixture was cooled and a small portion of aqueous sodium hydroxide was added. After the mild exotherm subsided, the remainder of 2 L of 1.5 N NaOH was added. This mixture was stirred 20 minutes and then the aqueous phase was removed. The organic phase was washed with salt water, then with HCl/salt water. The aqueous phases were extracted with methylene chloride (CH$_2$Cl$_2$) and the organic phase returned to the bulk organic phase each time. The combined methylene chloride extracts were concentrated on a rotary evaporator. The resulting black organic phase was continuously extracted with hexane until the black residue became very thick. The hexane extracts were concentrated under vacuum (60° C./0.2 Torr) to remove excess anisole. The remaining orange-red tetrapropyldithiomalonamide,

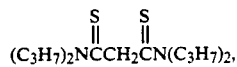

wt. 598 g (75% yield), was about 90% pure and contained about 1.5 wt. % anisole and 8 wt. % of dipropylthioacetamide (from acid catalyzed degradation of the malonyl groups).

Electrochemical fluorination of 597 g of this sample of N,N,N',N'-tetrapropyldithiomalonamide produced 800 g of crude cell drainings. A 335 g sample was stirred with 50 g of NaF and filtered yielding 307.2 g of a very lightly yellow colored fluid. This fluid was distilled at atmospheric pressure and fractionated. Those fractions boiling between 195°-217° C., 217°-218° C. and 238°-280° C. were collected. These fractions were separately treated with boiling aqueous alkali providing samples 1, 2 and 3, respectively. G.c. on these materials showed a major component with the retention time expected for (C$_3$F$_7$)$_2$NCF$_2$CF$_2$CF$_2$N(C$_3$F$_7$)$_2$. Elemental analyses for nitrogen (Kjeldahl) and sulfur gave values of 2.9% N and 0.46% S and 2.1% N and 0.36% S for samples 1 and 2, respectively. The theoretical elemental analysis for C$_{15}$F$_{34}$N$_2$ is 3.3% N and 0% S.

Sample 2 was further distilled. Distillation of 26 g of this fluid yielded 5.6 g having a boiling range of 200°-210° C., 5.8 g having a boiling range of 210°-212° C. and 3.7 g boiling at 212° C. $^{19}$F-nmr analysis of fluids having a boiling range of 210°-212° C. and boiling at 212° C. showed perfluoro[1,3-bis(di-n-propylamino)-propane], (C$_3$F$_7$)$_2$NCF$_2$CF$_2$CF$_2$N(C$_3$F$_7$)$_2$ as the major component. However, this component represented less than half of the mixture. Low field multiplets assigned to the sulfur bonded fluorines of R$_f$SF$_5$ were detected in $^{19}$F-nmr spectra of the sample. This result and the sulfur elemental analyses on Sample 2 are consistent with approximately one sulfur atom remaining per ten perfluorodiamine molecules. Viscosity measurements on combined material boiling at 200°-210° C. and 210°-212° C. showed the viscosity to be 9.1 centistokes at 22.5° C.

EXAMPLE 5

N,N,N', N'-tetrabutyldithiomalonamide,

was prepared by the method described in Example 4 except that N,N,N'N'-tetrabutylmalonamide was used in place of the tetrapropylmalonamide. A more volatile side product (presumably dibutylthioacetamide) was removed by evacuating to 0.3 Torr at 145° C.

Electrochemical fluorination of 927 g of the N,N,N',N'-tetrabutyldithiomalonamide produced 1230 g of crude cell drainings. G.c. on the crude cell drainings showed 12% of the integration in the boiling range for C$_{18}$-C$_{19}$ perfluroinated amines and 4% of the integration area for C$_{15}$-C$_{16}$ perfluorinated amines. Crude cell drainings were treated with sodium fluoride to remove HF and then with a boiling aqueous alkali solution to remove partially fluorinated products.

The resulting product was subjected to steam distillation. About 5% of the product recovered was found to be perfluoro[1,3-bis(di-n-butylamino)propane, (C$_4$F$_9$)$_2$NCF$_2$CF$_2$CF$_2$N(C$_4$F$_9$)$_2$, having a boiling range of 270°-280° C. as estimated by gas chromatography. About 16-18% of the product recovered was C$_{16}$F$_{36}$N$_2$ material, products resulting from carbon-carbon bond cleavage.

EXAMPLE 6

A 5 L flask was charged with 800 mL of water, 176 g of sodium hydroxide, 1200 mL of toluene, and 480 g of dipropylamine. This mixture was stirred slowly and cooled to 15°-20° C. as 394 g (2.5 mol) of adipoyl chloride was dripped in over 1 hour. After standing overnight, the organic phase was washed twice with acidified water. Distillation (bulb-to-bulb) of 20 mL of the toluene solution gave 6 g, about 65% yield, of crystalline N,N,N',N'-tetrapropyladipamide b.p. 130° C/0.05 Torr, m.p. 47.5°-48.5° C. after the crystals were washed with ethanol and vacuum dried.

The crude toluene solution of N,N,N',N'-tetrapropyladipamide was diluted with toluene (1200 mL) and azeotropically distilled to remove water. Dry toluene was added to replace distilled toluene. The solution was cooled to 70° C. and 300 g of phosphorous pentasulfide (99%, Aldrich Chemical Co., Milwaukee, WI) was slowly added. The temperature rose to 80° C. and was maintained there for 3 hours. Thin layer chromatography showed no amide and only a trace of monothioamide at this time. The reaction mixture was cooled and 600 g of 42% aqueous KOH was slowly added maintaining the tempurture below 31° C. After stirring overnight, the mixture was warmed and the organic phase was washed once with 1N NaOH and twice with water. The toluene solution was distilled again to remove water and on cooling to 0° C. yielded 247 g of tan tetrapropyldithioadipamide,

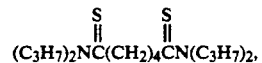

m.p. 88°-88.5° C. A second portion, 152 g, m.p. 87°-88° C., was collected from the mother liquor by concentrating and recrystallizing the residue from ethanol. Total yield was 399 g (78%), 51% overall yield from adipoyl chloride.

Electrochemical fluorination of 434 g of the

N,N,N',N'-tetrapropyldithioadipamide yielded 867 g of product (68% of theory). A 100 g sample of the crude cell drainings was stirred with sodium fluoride, filtered and treated with an aqueous caustic solution. A total of 16.7 g of perfluoroamine phase was collected by steam distillation.

Distillation of 37.8 g of a perfluoroamine phase similarly obtained through a 6-inch packed column yielded 5.58 g product having a boiling range of 249°–254° C. (Fraction 1), 4.35 g of product having a boiling range of 254°–255° C. (Fraction 2), 3.1 g product boiling above 255° C. (Fraction 3), as well as product boiling below 249° C. $^{19}$F-nmr analysis on fractions 1–3 showed only minor differences. These spectra were consistent with perfluoro-1,6-bis-(dipropylamino)hexane, $(C_3F_7)_2N(CF_2)_6N(C_3F_7)_2$, as the major component, about 70% of the mixture.

Combined fractions 1 and 2 were evaluated for various properties which are set forth in Table 3.

TABLE 3

| | |
|---|---|
| Boiling range | 249–255° C. |
| Viscosity | 29 c.s.*/22.5° C. |
| | 208 c.s./0° C. |
| | 40.5 c.p.*/25° C. |
| | 21 c.p./37.5° C. |
| Major component | $(C_3F_7)_2N(CF_2)_6N(C_3F_7)_2$ |
| | (about 70% by $^{19}$F-nmr) |
| | CF$_3$ |
| Minor component | $(C_3F_7)_2N(CF_2)_6NC_3F_7$ |
| | (about 20% by g.c.) |
| Total branched isomers with a tertiary perfluorocarbon atoms | (about 10% by nmr) |
| Perfluoroisobutylene release, microg/g-hr (time at 250° C.) | 0.97 (1 hr) |
| | 0.69 (2 hr) |

*c.s. - centistokes
c.p. - centipoise

EXAMPLE 7

N,N-dipropyl-p-toluamide (400 g) was diluted with toluene (2L). The solution was stirred at 80° C. and 164 g of phosphorus pentasulfide (99%, Aldrich Chemical Co., Milwaukee, WI) was slowly added. The temperature was maintained at 80° C. for 1 hour. Tlc showed no amide and only a trace of monothioamide at this time. The reaction mixture was decanted from the phosphorous derived phase and washed three times with basic water. The toluene solution was distilled at 0.1 Torr to a bath temperature of 100° C. leaving a residue of 370 g (84% yield) of oily red thioamide, N,N-dipropylthio-p-toluamide,

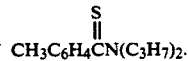

Electrochemical fluorination of 370 g of N,N-dipropylthio-p-toluamide produced 810 g of cell drainings. A 247 g sample was treated with sodium fluoride to remove HF and then treated with refluxing aqueous alkali solution. After 5.5 hours of refluxing, the perfluoroamine was steam distilled to yield 106.5 g of perfluoroamine phase. A total of 102 g of the perfluoroamine product was then distilled through a 16-inch Vigreux column and fractionated. Those fractions boiling between 170°–205° C. and 205°–215° C. were collected.

Gas chromatography indicated that 56% of the fraction boiling between 170°–205° C. and 92% of the fraction boiling between 204°–215° C. were the desired $C_{14}F_{29}N$, i.e., $CF_3C_6F_{10}CF_2N(C_3F_7)_2$, or closely related species. The $^{19}$F-nmr spectrum of the fraction boiling between 205°–215° C. was complex, showing that less than 50% of the $N(CF_2CF_2CF_3)$ groups remained. Bicyclic structures, $C_{14}F_{27}N$, where the propyl groups have cyclized onto the carbons of the original aromatic ring and closely related species are likely structures for the major products. The product of the fraction boiling between 205°–215° C. had viscosities of 51.5 c.p. at 0° C. and 12.7 c.p. at 25° C.

EXAMPLE 8

A 5 L flask was charged with 670 g of terephthaldimorpholine amide and 2.2 L of trichloroethylene. This mixture was briefly distilled to remove water, then was refluxed as a total of 1500 g of phosphorous pentasulfide was added in portions. This mixture was refluxed 24 hours. The solid product (containing excess phosphorus derived solids) was collected by filtration of the cooled reaction mixture. These solids were then carefully added in portions to a well-stirred solution of 1500 g of NaOH in 2 L of water at 50°–80° C. The solids remaining undissolved were filtered and washed with water giving 641 g (87% yield) of dithioterephthaldimorpholine amide,

(para isomer).

Electrochemical fluorination of 511 g of the dithioterephthaldimorpholine amide produced 561 g of viscous crude cell drainings. A portion of the crude cell drainings was treated with sodium fluoride to yield 76 g of material which was then refluxed with aqueous alkali to remove HF and partially fluorinated by-products. Viscous oily perfluoroamine product 21.4 g was obtained which partially crystallized on standing. Filtration of the crystals (m.p. 70°–80° C. and recrystallization from cold Freon-11$^R$ gave needles melting at 73°–79.5° C. The $^{19}$F-nmr spectrum of these needles showed five signals at $-80.7$, $-88.1$, $-92.7$, $-121.1$ and $-180.9$ ppm consistent with the trans isomer of $O(C_2F_4)_2NCF_2C_6F_4CF_2N(C_2F_4)_2O$, i.e.,

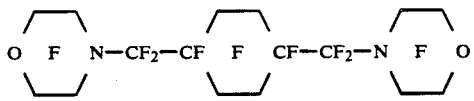

A boiling point of 250°–270° C. was estimated using g.c. retention behavior for this material.

EXAMPLE 9

A 5 L flask was charged with 390.7 g isophthaloyl dichloride and 1L of toluene. This mixture was stirred under nitrogen atmosphere as 780 g of dipropylamine was added in over 3- hours. The organic phase was washed with water, 13% aqueous sodium hydroxide, 10% aqueous hydrochloric acid, and water. Distillation (bulb-to-bulb) of 14.7 g of the toluene solution gave 5.3 g, about 91% yield, of viscous amide distillate. A 315 g portion of the crude toluene solution of N,N,N',N'-tetrapropyl isophthalamide (containing about 113.4 g isothalamide) was diluted with toluene (200 mL) and azeotropically distilled to remove water. Dry toluene was added to replace distilled toluene. The solution was cooled to 80° C. and 52.4 g of phosphorus pentasulfide (99%, Aldrich Chemical Co., Milwaukee, WI) was slowly added. The temperature rose to 90° C. and was maintained there for 1 hour. Infrared analysis showed no amide functionality remaining at this time. The reaction mixture was cooled and washed once with 1N NaOH and twice with water. The toluene solution was concentrated and the residue was recrystallized from ethanol to yield 89.6 g of light yellow crystals of N,N,N',N'-tetrapropyldithioisophthalamide,

meta isomer, m.p. 83.5°–85.0° C.

Electrochemical fluorination of 50 g of the N,N,N',N'-tetrapropyldithioisophthalamide gave viscous cell drainings which were diluted in FC-77, a perfluorinated inert liquid available from 3M Company, to facilitate handling. This solution was stirred with NaF and filtered. The filtrate was distilled to a pot temperature of 250° C. leaving 58.1 g of undistilled residue. The residue (52.2 g) was refluxed with aqueous alkali solution to remove partially fluorinated materials. Volatile perfluorinated product evaporated. Steam distillation of the residue yielded 14.7 g of viscous perfluoroamine product. Of this, 13.2 g was distilled giving fractions as follows:

| Fraction | Boiling range(°C.) | Weight (g) | Viscosity (c.p. 25° C.) | Comments |
|---|---|---|---|---|
| 1 | 60–255 | ca. 2 | | |
| 2 | 255–260 | 2.44 | 156 | Clear, colorless |
| 3 | 260–268 | 2.89 | 371 | Clear, colorless |
| 4 | 268–272 | 4.14 | 1455 | Slightly cloudy and very light amber in color |

EXAMPLE 10

N,N'-Di(thiobenzoyl)piperazine was prepared as described by Chabrier, P. et al. in *Bull. Chim. Soc. Fr.*, 1950, pp 1167–1175. Electrochemical fluorination of 500 g of the N,N'-di(thiobenzoyl)piperazine yielded 577 g of crude cell drainings. G.c. analysis on this product indicated the presence of predominantly low boiling fluorocarbon compounds containing six and eight carbon atoms. F$^{19}$ nmr indicated the presence of perfluoro(methylcyclohexane) and perfluoro(dialkylpiperazine) structures. About 2–3% of the product is high-boiling compounds (b.p. >250° C.) that contain the original number of carbon atoms, i.e., eighteen.

Various modifications and alterations of this invention will become apparent to those skilled in the art without departing from the scope and spirit of this invention, and it should be understood that this invention is not to be unduly limited to the following illustrative embodiments set forth herein.

I claim:

1. A process for preparing tertiary perfluoroamines comprising electrochemically fluorinating a tertiary thioamide precursor, said thioamide precursor comprising at least one thioamide moiety,

and terminal portions which can be alkyl or cycloalkyl having 1 to 12 carbon atoms, aryl having 6 to 12 carbon atoms, or combinations thereof, with the proviso that when more than one thioamide moiety is present, the thioamide moieties are bonded together by alkylene, cycloalkylene or arylene groups.

2. The process of claim 1 wherein said thioamide precursor is represented by the formula

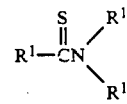

wherein each R$^1$ is independently alkyl, cycloalkyl, aryl or a combination thereof which can contain catenary oxygen atoms or two R groups attached to the same nitrogen atom can be joined to form a ring having 4 to 10 carbon atoms and which can contain a catenary oxygen atom.

3. The process of claim 1 wherein said thioamide precursor is represented by the formula

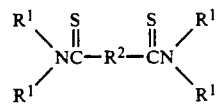

wherein
each R$^1$ is independently alkyl, cycloalkyl, aryl or a combination thereof which can contain catenary oxygen atoms or two R$^1$ groups attached to the same nitrogen atom can be joined to form a ring having 4 to 10 carbon atoms and which can contain a catenary oxygen atom; and
R$^2$ is an alkylene, cycloalkyl, arylene or combination thereof which can contain one or more tertiary amino groups.

4. The process of claim 1 wherein said thioamide precursor is represented by the formula

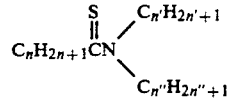

wherein n, n', and n" are independently integers of from 1 to 10.

5. The process of claim 1 wherein said thioamide precursor is represented by the formula

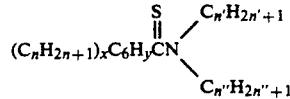

wherein n, n', and n" are independently integers of from 1 to 10; x is 0 to 5; y is 0 to 5; and x+y is 5.

6. The process of claim 1 wherein said thioamide precursor is represented by the formula

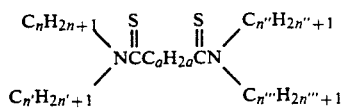

wherein n, n', n'', and n''' are independently integers of from 1 to 10 and a is an integer of from 1 to 10.

7. The process of claim 1 wherein said thioamide precursor is represented by the formula

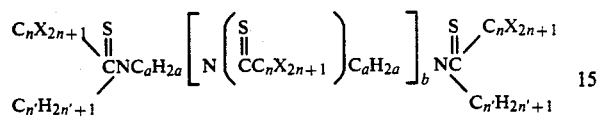

wherein X is H or F, n, n', n'', and n''' are independently integers of from 1 to 10, a is an integer of from 1 to 10, and b is 0, 1 or 2.

8. The process of claim 1 wherein said thioamide precursor is represented by the formula

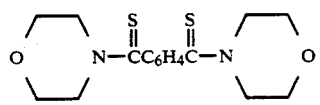

9. The process of claim 1 wherein said thioamide precursor is represented by the formula

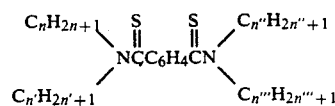

wherein n, n', n'', and n''', are independently integers of from 1 to 10.

10. The process of claim 1 wherein said thioamide precursor is represented by the formula

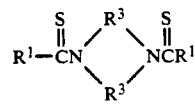

wherein
each $R^1$ is independently alkyl, cycloalkyl, aryl or a combination thereof which can contain catenary oxygen atoms or two $R^1$ groups attached to the same nitrogen atom can be joined to form a ring having 4 to 10 carbon atoms and which can contain a catenary oxygen atom; and
$R^3$ is alkylene containing 1 to 10 carbon atoms.

11. The process of claim 1 wherein said thioamide precursor is represented by the formula

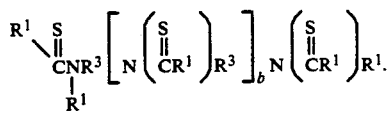

wherein
each $R^1$ is independently alkyl, cycloalkyl, aryl or a combination thereof which can contain catenary oxygen atoms or two $R^1$ groups attached to the same nitrogen atom can be joined to form a ring having 4 to 10 carbon atoms and which can contain a catenary oxygen atom;
$R^2$ is an alkylene, cycloalkylene, arylene or combination thereof having 1 to 10 carbon atoms which can contain one or more tertiary nitrogen atom;
$R^3$ is alkylene containing 1 to 10 carbon atoms;
b is 0, 1 or 2.

12. The process of claim 1 wherein said thioamide precursor is represented by the formula

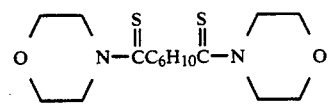

13. The process of claim 1 wherein said thioamide precursor is represented by the formula

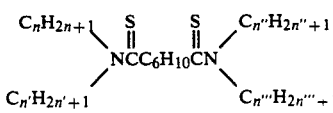

wherein n, n', n'', and n''' are independently integers of from 1 to 10.

14. The process of claim 1 wherein said thioamide precursor is represented by the formula

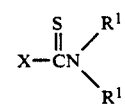

wherein X is H, F or R' and $R^1$ is as defined above.

15. The process of claim 1 wherein said thioamide precursor is represented by the formula

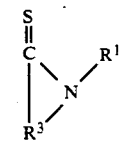

wherein $R^1$ is as defined above and $R^3$ is alkylene containing 1 to 10 carbon atoms.

16. The process of claim 1 wherein said thioamide precursor is represented by the formula

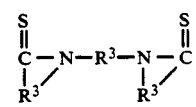

wherein each $R^3$ is alkylene containing 1 to 10.

17. The process of claim 1 wherein said thioamide precursor is represented by the formula

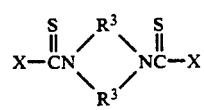

wherein $R^3$ and X are as defined above.

18. The process of claim 1 wherein said thioamide precursor is represented by the formula

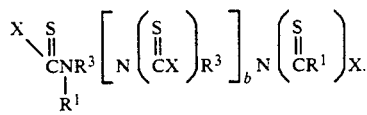

wherein $R^1$, $R^3$, and b are as defined above and X is H, F or $R^1$.

19. The process of claim 1 wherein said thioamide precursor is represented by the formula

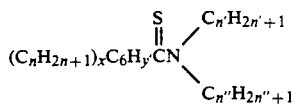

wherein n, n', and n'' are independently integers of from 1 to 10; x is 0 to 5; y'is 0 to 11; and x+y' is 11.

20. A process for preparing tertiary perfluoroamines comprising electrolyzing for a period of hours a current-conducting mixture of liquid hydrogen fluoride free from water in more than a small proportion and a thioamide precursor comprising at least one thioamide moiety,

and terminal portions which can be alkyl or cycloalkyl having 1 to 12 carbon atoms, aryl having 6 to 12 carbon atoms, or combinations thereof, with the proviso that when more than one thioamide moiety is present, the thioamide moieties are bonded together by alkylene, cycloalkylene or arylene groups, at a temperature and pressure at which a liquid state is maintained and at a cell voltage which is insufficient to generate free fluorine under the existing conditions but which is sufficient to cause the production of tertiary perfluoroamines at a useful rate, and recovering tertiary perfluoroamine product.

21. A process for preparing tertiary perfluoroamines comprising electrolyzing in a nickel-anode cell a current-conducting mixture of anhydrous liquid hydrogen fluoride and a thioamide precursor comprising at least one thioamide moiety,

and terminal portions which can be alkyl or cycloalkyl having 1 to 12 carbon atoms, aryl having 6 to 12 carbon atoms, or combinations thereof, with the proviso that when more than one thioamide moiety is present, the thioamide moieties are bonded together by alkylene, cycloalkylene or arylene groups, by passing direct current through the mixture for a period of hours at an electrolyzing potential which is insufficient to generate free fluorine under the existing conditions but which is sufficient to cause the production of tertiary perfluoroamines at a useful rate, the temperature and pressure being such as to maintain a liquid state, and recovering tertiary perfluoroamine product.

22. A process for preparing tertiary perfluoroamines comprising electrolyzing for a period of hours a current-conducting solution essentially consisting of liquid hydrogen fluoride containing a dissolved conductivity additive and a thioamide precursor comprising at least one thioamide moiety,

and terminal portions which can be alkyl or cycloalkyl having 1 to 12 carbon atoms, aryl having 6 to 12 carbon atoms, or combinations thereof, with the proviso that when more than one thioamide moiety is present, the thioamide moieties are bonded together by alkylene, cycloalkylene or arylene groups, and which is free from water in more than a small proportion, at a temperature and pressure at which a liquid state is maintained and at an electrolyzing potential which is insufficient to generate free fluorine under the existing conditions but which is sufficient to cause the production of tertiary perfluoroamines at a useful rate, and recovering tertiary perfluoroamine product.

* * * * *

UNITED STATES PATENT AND TRADEMARK OFFICE
CERTIFICATE OF CORRECTION

PATENT NO. : 5,108,556
DATED : April 28, 1992
INVENTOR(S) : Jack E. Richman

PAGE 1 OF 2

It is certified that error appears in the above-identified patent and that said Letters Patent is hereby corrected as shown below:

Col. 4, line 26    "b + 2SF$_6$" should read -- (b + 2) SF$_6$ --

Col. 4, line 41    "R$^1$" should read -- R$_f^1$ --

Col. 4, line 42    "R$_f$" should read -- R$_f^3$ --

Col. 5, line 42    " H or f " should read -- H or F --

Col. 7, line 15    "for hours" should read -- for 5 hours --

Col. 7, line 51    "CF$_3$CF$_2$N(C$_3$F$_{76}$)$_2$," should read -- CF$_3$CF$_2$N(C$_3$F$_7$)$_2$, --

Col. 9, line 33    add "." at end of line

Col. 10, formulas at lines 5, 20, 32 and 47

$$\text{"}\quad C_3H_7 - \left( \begin{array}{c} CF_3CF_2 \\ | \\ -NC_3H_6- \end{array} \right)_3 - F \quad\text{"}$$

should read

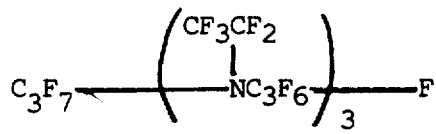

UNITED STATES PATENT AND TRADEMARK OFFICE
CERTIFICATE OF CORRECTION

PATENT NO. : 5,108,556
DATED : April 28, 1992
INVENTOR(S) : Jack E. Richman

PAGE 2 OF 2

It is certified that error appears in the above-identified patent and that said Letters Patent is hereby corrected as shown below:

Col. 13, lines 27-28

"$CF_3$
Minor component    $(C_3F_7)_2N(CF_2)_6NC_3F_7$ "
should read

--                                  $CF_3$
Minor component    $(C_3F_7)_2N(CF_2)_6NC_3F_7$ --

Col. 14, line 60    "3-" should read -- 3 --

Col. 16, line 42    "cycloalkyl," should read -- cycloalkylene --

Col. 16, line 66    "✗" should read -- x --

Col. 18, lines 3-5    delete lines 3-5 beginning with "$R^2$" and ending with "atom;"

Col. 18, line 35    "R'" should read -- $R^1$ --

Signed and Sealed this

Twenty-fourth Day of August, 1993

*Attest:*

BRUCE LEHMAN

*Attesting Officer*    *Commissioner of Patents and Trademarks*